(12) United States Patent
Emilie et al.

(10) Patent No.: US 8,198,235 B2
(45) Date of Patent: Jun. 12, 2012

(54) USE OF GILZ PROTEIN EXPRESSED IN DENDRITIC CELLS TO MODULATE AN ANTIGEN-SPECIFIC IMMUNE RESPONSE

(75) Inventors: Dominique Emilie, Paris (FR); Nicolas Cohen, Saint-Mandé (FR); François Lemoine, Montrouge (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 870 days.

(21) Appl. No.: 11/575,073

(22) PCT Filed: Sep. 9, 2005

(86) PCT No.: PCT/FR2005/002247
§ 371 (c)(1),
(2), (4) Date: Mar. 27, 2008

(87) PCT Pub. No.: WO2006/030118
PCT Pub. Date: Mar. 23, 2006

(65) Prior Publication Data
US 2009/0028875 A1    Jan. 29, 2009

(30) Foreign Application Priority Data
Sep. 10, 2004 (FR) ...................... 04 09620

(51) Int. Cl.
*A61K 48/00* (2006.01)
(52) U.S. Cl. .............. 514/2; 435/325; 435/375

(58) Field of Classification Search ............ None
See application file for complete search history.

(56) References Cited

U.S. PATENT DOCUMENTS

| | | | |
|---|---|---|---|
| 2003/0154032 A1* | 8/2003 | Pittman et al. | 702/20 |
| 2004/0146492 A1* | 7/2004 | Hwu et al. | 424/93.21 |
| 2004/0161417 A1* | 8/2004 | Gilboa et al. | 424/93.21 |
| 2004/0194160 A1* | 9/2004 | Riccardi | 800/18 |

FOREIGN PATENT DOCUMENTS

WO   03 054193   7/2003

OTHER PUBLICATIONS

Berrebi, et al., "Synthesis of Glucocorticoid-induced Leucine Zipper (GILZ) by Macrophages: an Anti-inflammatory and Immunosuppressive Mechanism Shared by Glucocorticoids and IL-10", Blood, vol. 101, No. 2, pp. 729-738, 2003.

* cited by examiner

*Primary Examiner* — Kimberly Chong
(74) *Attorney, Agent, or Firm* — Oblon, Spivak, McClelland, Maier & Neustadt, L.L.P.

(57) ABSTRACT

The invention concerns the use of at least one: a) a GILZ protein, a functional fragment of at least 5 consecutive amino acids of said protein, a GILZ modulator, or a recombinant vector expressing same, isolated or expressed in modified dendritic cells, and b) an antigen of interest and/or a molecule allowing targeting and/or passage of the plasmic membrane of dendritic cells, to prepare a medicine for preventing and/or treating autoimmune, inflammatory diseases, allergies, graft rejection and graft-versus-host disease, cancers and pathogenic micro-organism infections.

6 Claims, 4 Drawing Sheets

Figure 1:
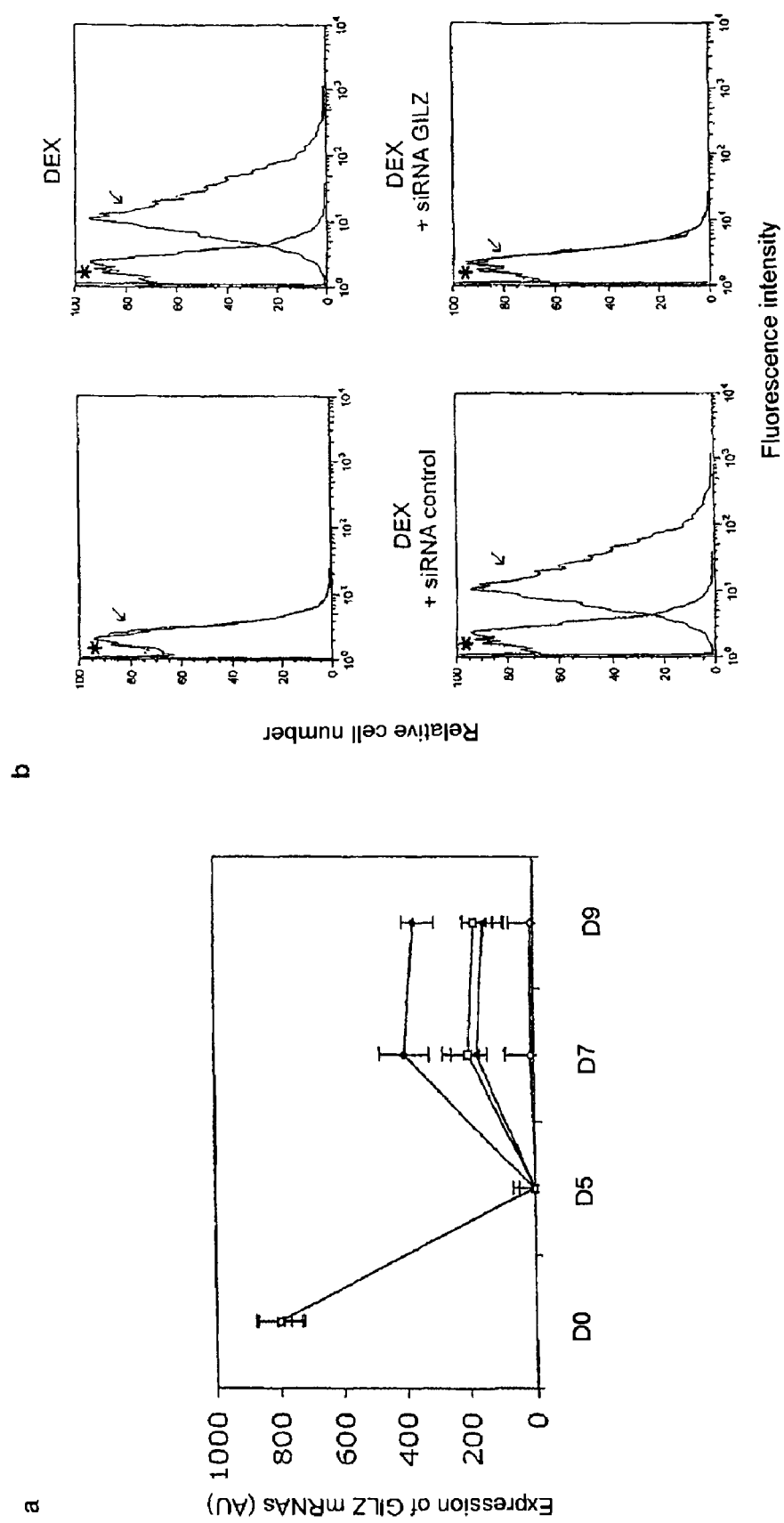

USE OF GILZ PROTEIN EXPRESSED IN DENDRITIC CELLS TO MODULATE AN ANTIGEN-SPECIFIC IMMUNE RESPONSE

The present invention relates to the use of the GILZ protein or of an agent or agents for modulating the effects of said GILZ protein, expressed in dendritic cells, for the purpose of either inducing regulatory/suppressor T lymphocytes so as to generate immune tolerance, in particular in the treatment of autoimmune diseases, inflammatory diseases, allergies, transplant rejection and graft-versus-host disease, or, on the contrary, of inhibiting the regulatory/suppressor T lymphocytes present so as to put an end to a state of tolerance, in particular in the treatment of cancer or of chronic infections, or so as to induce an effective immune response against a vaccine antigen.

Dendritic cells (DCs) are conventionally described as being the best antigen-presenting cells for T lymphocytes. Indeed, dendritic cells are capable of presenting peptide antigens, via the molecules of the class I and class II major histocompatibility complex (MHC I and MHC II) to $CD8^+$ and $CD4^+$ T lymphocytes, respectively, and of inducing, after activation, an effective immune response. More recent data indicate that, under the effect of various physiological factors and/or of pharmacological agents, dendritic cells are, on the contrary, capable of inhibiting T lymphocyte activation and thus of inducing a state of tolerance. Immune tolerance results from two processes: the induction of responder-cell energy or apoptosis and the generation of T lymphocytes having suppressor functions (regulator/suppressor T lymphocytes).

Regulatory/suppressor T lymphocytes play a major role both physiologically and in pathological situations, such as autoimmune diseases, allergies, transplant rejection, chronic infections and malignant proliferations (Hisaeda et al., Nat. Med., 2004, 10, 29-.; Lundgren et al., Infect. Immun., 2003, 71, 1755-; Hasenkrug, Novartis Found. Symp., 2003, 252, 194-; Boyer et al., Blood, 2004, 103, 3428-3430; Woo et al., Cancer Res., 2001, 61, 4766-; Sasada et al., Cancer, 2003, 98, 1089-; Wolf et al., Clin. Cancer Res., 2003, 9, 606-; Ichihara et al., Clin. Cancer Res., 2003, 9, 4404; Salomon et al., Immunity. 2000, 12, 431; Takahashi. Curr. Top. Med. Chem., 2003, 3, 693-; Xu et al., J. Immunol; 2003, 170, 394-).

Three populations of regulatory/suppressor T lymphocytes have been described to date: i) Th3 cells, which are $CD4^+$ $CD25^-$, produce Transforming Growth Factor beta (TGFβ), interleukin (IL)-10 and IL-4 while at the same time having a suppressor action via a TGFβ dependent mechanism (Weiner et al., Immunol. Rev., 2001, 182, 207-); ii) type 1 regulatory T cells (Tr1), which also represent a $CD4^+$ subpopulation, produce IL-10 and TGFβ but use IL-10 for their differentiation and their suppressor function (Groux, Transplantation, 2003, 75, 85-; Levings et al., J. Exp. Med., 2002, 196, 133); iii) $CD4^+CD25^{high}$ cells (Treg), the suppressor action of which, initiated after an antigen-specific activation via the T cell receptor (TCR), is exerted in an antigen-independent manner by inhibiting the production of IL-2, and promoting cell-cycle arrest in $CD4^+$ and $CD8^+$ cells via a mechanism involving cell contact, and partially TGFβ but not IL-10 (Sakaguchi et al., Immunol. Rev., 2001, 182, 18-; Shevach, Nat. Rev. Immunol., 2002, 2, 389-).

Although the phenotype, the cytokine expression profile and the suppressor mechanisms of Th3, Tr1 and Treg lymphocytes have been characterized, the interaction of regulatory/suppressor lymphocytes with dendritic cells and the role of this interaction in the induction/inhibition of regulatory/suppressor lymphocytes is poorly understood. It has been shown that treating the dendritic cells with corticosteroids or IL-10 induces T lymphocytes having suppressor functions (Hackstein et al., mentioned above; Steinman et al., Ann. Rev. Immunol., 2003, 21, 685-711; Ashworth et al., Eur. J. Immunol., 2000, 30, 1233-1242; Muller et al., J. Invest. Dermatol, 2002, 119, 836-841; Steinbrink et al., Blood., 2002, 99, 2468-2476; Akbari et al., Nat. Immunol., 2001, 2, 725-731). However, the genes capable of inducing or, on the contrary, of inhibiting antigen-specific regulatory T lymphocytes, representing therapeutic targets for modulating regulatory/suppressor T lymphocytes, have not been identified.

Enhancing man's knowledge of the induction and inhibition of regulatory/suppressor T lymphocytes would make it possible to envision their therapeutic use, either for promoting or inducing a state of intolerance for the purpose of treating autoimmune diseases, inflammatory diseases or allergies, or for controlling graft-versus-host disease or transplant rejection in the context of allogenic transplants, or, on the contrary, for inducing a better immune response against a tumor antigen, an antigen responsible for chronic infection or a vaccine antigen, by inhibiting them.

The gene encoding the GILZ (Glucocorticoid-Induced Leucine Zipper) protein has been cloned from murine T lymphocytes and thymocytes cultured in the presence of glucocorticoids. The murine GILZ protein and its human homolog correspond, respectively, to the SWISSPROT sequences Q9Z2S7 and Q99576 and the cDNAs encoding said proteins correspond to the GenBank sequences AF024519 and AF228339. In these cells, GILZ inhibits cell death (apoptosis induced by activation of the T receptor for the antigen (D'Adamio et al., Immunity, 1997, 7, 803)). GILZ is also induced by glucocorticoids in human B lymphocytes and macrophages (Berrebi et al., BLOOD, 2003, 101, 729-738). In B lymphocytes, GILZ inhibits the activation via the B receptor for the antigen (Glynne et al., Immunol. Rev., 2000, 176, 216-). In macrophages, GILZ acts at least in part by blocking monocyte activation induced by bacterial extracts (LPS) or activators of T lymphocyte origin (CD40L, IFN-gamma) and inhibits the production of proinflammatory chemokines and costimulatory molecules CD80 and CD86 (Berrebi et al., mentioned above). In addition, a disturbance in the expression of GILZ in macrophages is observed in inflammatory processes related to delayed hypersensitivity reactions (repression of GILZ in Crohn's disease, or in tuberculosis) and in tumors (persistence of GILZ expression over the course of Burkitt's lymphoma). GILZ expression can also be induced in other cell types, by various stimulants: aldosterone and vasopressin in murine kidney tubule cells (Robert-Nicoud et al., P.N.A.S., 2001, 98, 2712-), or mesenchymal cells (Shi et al., EMBO Rep., 2003, 4, 374-).

The regulation of GILZ production includes sites for binding of the glucocorticoid receptor to its promoter, and the presence of cofactors of the Sonic Hedgehog family (Ingram et al., Oncogene, 2002, 21, 8196-) or of the Forkhead family (Asselin-Labat et al., Blood, 2004, 104, 215-223). The effects of GILZ seem to be exerted on several cell activation pathways: the NF-KB pathway (Riccardi et al., Adv. Exp. Med. Biol., 2001, 495, 31-), the AP-1 pathway (Mittelstadt et Ashwell, J. Biol. Chem., 2001, 276, 29603-), the MAP kinase pathway Ayroldi et al., Mol. Cell. Biol., 2002, 22, 7929-).

It has in particular been shown that the GILZ protein is a MAP kinase pathway inhibitor capable of blocking Raf/Ras-mediated signal transduction, that can be used for inhibiting the cell proliferation associated with cancer, with autoimmune diseases, with inflammatory pathologies and with transplant rejection (PCT International Application WO 03/054193).

The inventors have demonstrated new properties of the GILZ protein, associated with its expression in cells other than those mentioned above, making it possible to envision new uses of the GILZ protein.

The inventors have shown that GILZ expression extinguishes over the course of the differentiation of dendritic cell precursors (CD34+ or monocytes) to immature dendritic cells (iMDDCs) and that activation of the dendritic cells with CD40L, which allows maturation thereof, does not restore this production. However, the induction of GILZ expression in immature dendritic cells (iMDDCs) or mature dendritic cells (MDDCs) promotes the tolerance-inducing functions of dendritic cells and inhibits their immunostimulatory functions. The tolerance-inducing action of GILZ is exerted through the induction of antigen-specific suppressor T lymphocytes and the production of GILZ by dendritic cells is essential for these cells to generate suppressor T lymphocytes.

Thus, the modulation of the production or of the function of the GILZ protein in dendritic cells during antigen presentation, by virtue of its effects on the production of suppressor T lymphocytes, makes it possible to dictate the quality of the response to this antigen.

The demonstration of the action of the GILZ protein on antigen-presenting cells and of its effect on the induction of regulatory/suppressor T lymphocytes makes it possible to envision the use of GILZ (protein, functional peptide fragment or corresponding cDNA included in a recombinant expression vector) or of a GILZ modulator (activator or inhibitor), for modulating the antigen-specific immune response. The use of GILZ and/or of a GILZ activator, isolated or expressed in dendritic cells modified with the cDNA or the corresponding protein, makes it possible to induce tolerance to this antigen, for the purpose of treating autoimmune diseases, inflammatory diseases or allergies, or of controlling transplant rejection and graft-versus-host disease in the context of allogenic transplants. The use of a GILZ inhibitor, isolated or expressed in dendritic cells modified with the cDNA or the corresponding protein, makes it possible, on the contrary, to inhibit the regulatory/suppressor T lymphocytes present so as to put an end to a state of tolerance, in particular in the treatment of cancer or of chronic infections, or to induce an effective immune response against a tumor antigen or an antigen of a pathogen, in the context of an anti-tumor or anti-infective vaccination.

Consequently, a subject of the present invention is the use of at least:
a) a GILZ protein, a functional fragment of at least 5 consecutive amino acids of said protein, a GILZ modulator, or a recombinant expression vector for the above, isolated or expressed in modified dendritic cells, and
b) an antigen of interest and/or a molecule for targeting and/or crossing the plasma membrane of dendritic cells,
for preparing a medicament for use in the prevention and/or treatment of autoimmune diseases, inflammatory diseases, allergies, transplant rejection and graft-versus-host disease, cancers and pathogenic microorganism infections.

DEFINITIONS

The term "GILZ protein" is intended to mean a GILZ protein from any mammal. The human GILZ protein and its murine homolog correspond, respectively, to the SWISSPROT sequences Q99576 and Q9Z2S7, and the cDNAs encoding said proteins correspond to the GenBank sequences AF228339 and AF024519. The sequence of the GILZ protein of other mammals can be determined by cloning the corresponding cDNA, using primers chosen from the human and murine sequences, according to the conventional molecular biology techniques known to those skilled in the art.

The term "GILZ gene" is intended to mean the gene encoding the GILZ protein.

The expression "functional GILZ protein or functional fragment of the GILZ protein" is intended to mean a protein or a peptide of at least 5 consecutive amino acids of GILZ which, when it is expressed in antigen-presenting cells, is capable of generating antigen-specific regulatory/suppressor T cells. Fragments of the GILZ protein are in particular described in application WO 03/054193. The functionality of a GILZ protein or peptide as defined above can be evaluated by demonstrating the inhibition of the proliferation of antigen-specific $CD4^+$ T cells and/or $CD8^+$ T cells in the presence of autologous antigen-presenting cells.

The term "GILZ modulator" is intended to mean a GILZ activator or inhibitor.

The term "GILZ activator" is intended to mean an inducer or an activator of the expression of the GILZ gene or an activator of the function of the GILZ protein. Said inducer or activator of the expression of the GILZ gene can act either directly by stimulating the expression of GILZ, or indirectly by blocking the action of inhibitors of this expression. Said activator of the function of the GILZ protein is in particular a GILZ cofactor, a substance which acts on the phosphorylation, the glycosylation or the acylation of GILZ, or alternatively a substance that interferes with the synthesis or the function of a GILZ cofactor.

The term "GILZ inhibitor" is intended to mean an inhibitor of the expression of the GILZ gene or an inhibitor of the function of the GILZ protein; said inhibitor of the expression of the GILZ gene can act either directly, or indirectly by blocking the action of inducers or of activators of this expression.

The term "GILZ transcript" is intended to mean the mRNA encoding the GILZ protein.

The term "modified dendritic cells" is intended to mean dendritic cells, preferably autologous dendritic cells, in which an exogenous GILZ protein, a functional fragment of at least 5 consecutive amino acids of said protein, a GILZ modulator or a recombinant expression vector for said protein, for said fragment or for said GILZ modulator has been introduced by any means, known in itself, for introducing a substance into a target cell.

The expression "molecule for targeting and/or crossing the plasma membrane of dendritic cells" is intended to mean any molecule, known in itself, that makes it possible to specifically introduce a substance into dendritic cells. By way of nonlimiting example, mention may in particular be made of membrane peptides, lipids, ligands of a membrane receptor or of a surface antigen of dendritic cells, in particular peptides, and antibodies directed against: DC-SIGN, CD40, DEC-205, langerin, the mannose receptor or scavanger receptors. The DEC-205 membrane receptor is in particular described in Bonifaz et al., J. Exp. Med., 2004, 199, 815-824.

The invention encompasses modified GILZ proteins, in particular variants of GILZ and fragments of at least five consecutive amino acids of said proteins corresponding to a functional GILZ protein or peptide as defined above. The modifications which are introduced into the GILZ protein or peptide by conventional techniques known to those skilled in the art include, in a nonlimiting manner: mutation (insertion, deletion, substitution) of at least one amino acid in the GILZ sequence (production of GILZ variants), addition of a fusion sequence (production of a fusion protein), substitution of amino acid residues with unnatural amino acid residues (D amino acids or amino acid analogs), modification of the peptide bond, cyclization, addition of chemical groups on the amino acid side chains, coupling to a molecule of interest, in particular a molecule for targeting and/or crossing the plasma membrane of dendritic cells as defined above; said coupling is carried out by means of a noncovalent or covalent bond such as a peptide bond, in particular when the GILZ protein, a fragment of said protein or a GILZ modulator, which is protein in nature, is used with a peptide ligand of a membrane receptor or of a surface antigen of dendritic cells (production of a chimeric GILZ protein or peptide).

The GILZ modulators include, in particular: glucocorticoid or mineralocorticoid hormones (or derivatives thereof); sex hormones (estrogen, progesterone, androgen, or derivatives thereof); cytokines such as IL-10, IL-4, IL-13, TGF-beta or derivatives that act on their receptor; vitamin D and analogs thereof; natural chemokines and variants thereof; ligands of receptors such as the CCR5 receptor; recombinant proteins derived, for example, from CTLA4 or from LAG-3; immunoglobulins, polyclonal nonspecific or monoclonal; HLA-G and soluble, natural or recombinant forms thereof; substances that act on the immunoglobulin Fc fragment receptor; substances that interfere with the function of Toll-like receptors (TLRs), of CD36, of CD46, of complement receptors, of scavenger receptors (such as Lox-1 and MARCO), of the mannose receptor, of DC-SIGN, and of the phosphatidyl serine receptor. They may also be substances that interfere with the production or the function of intracellular mediators, and in particular the akt and PI3K kinases, and the PTEN, SHP and SHIP phosphatases, and the proteins of the Forkhead family, of the Smad family and of the STAT family (and in particular STAT3). They may also be immunosuppressor drugs such as cyclosporin, KF506, rapamycin, methotrexate, mycophenolate or azathioprine. They may be substances derived from infectious agents, in particular from *Plasmodium falciparum, Leishmania, Candida albicans, Klebsiella pneumoniae, Toxoplasma gondii, Trypanosoma cruzi, Mycobacterium tuberculosis, Porphyromonas gingivalis*, from HIV-derived viral proteins (such as vpr, gp41, gp120 and gp160), from the hepatitis B virus or the hepatitis C virus, from herpes viruses and from poxviruses.

The antigen which is used is in particular in the form of an antigenic preparation, prepared in particular from cells, from an isolated antigen (protein, peptide or derivative, or the like) or alternatively from a recombinant expression vector for said antigen.

The antigen which is used to induce immune tolerance is chosen from antigens which have been identified as being responsible for the pathology to be treated, i.e., in a nonlimiting manner:
autoantigens involved in autoimmune diseases such as: thyroiditis, diabetes, multiple sclerosis, peripheral neuropathy, celiac disease, Goodpasture's syndrome, polymyositis and dermatomyositis, atrophic polychondritis, antiphospholipid syndrome, vasculitis, autoimmune gastritis, autoimmune hemolytic anemia, autoimmune thrombopenic purpura, autoimmune hepatitis, phemphigus and pemphygoid, vitiligo, myasthenia, hemophilia, autoimmune angioneurotic edema. The autoantigens involved are in particular the following: basal membrane, TSH receptors, acetylcholine, beta 2-glycoprotein 1, C1-inactivator, desmosomes and hemidesmosomes, intrinsic factor, gangliosides, insulin and proinsulin, glutamate decarboxylase (GAD), islet antigen 2 (IA2), myelin-associated glycoprotein (MAG) and myelin basic protein, tyrosinase, prothrombin, calcium or potassium channels, thyroperoxidase, thyreglobulin and gliadin;

allergens: pollen (grass and cereal pollens (*Phleum pratense, Zea mays, Secale cereale, Avena sativa, Anthoxanthum odotarum, Poa pratensis, Phragmites australis, Triticum sativum, Lolium perenne*)), hymenoptera venom (Api m1 and m2: phospholipase A2 and hyaluronidase of *Apis mellifera*; Ves v 1, ves m 1, Pol a 1, Ves v 2, Ves m 2, Pol a 2 (phospholipase A1 and hyaluronidase of *vespula vulgaris, germanica* or yellow jacket), acarids (Der p 1, Der p 2, Der f 1), cat hair (Fel d 1), peanut (Ara h 1, 2 and 3), infectious agents such as *Aspergillus fumigatus*, birch, olive tree, flour, latex (Hev b 1 to 11), cod (gad c 1), shellfish and shrimp (Pen a 1), egg, cows' milk, and the recombinant proteins corresponding to these allergens;

antigens involved in chronic inflammatory diseases such as: psoriasis, rheumatoid arthritis and inflammatory diseases of the digestive tract;

transplantation antigens involved in transplant rejection and graft-versus-host disease, for instance the antigens of the major histocompatbility complex (MHC, or HLA in humans) and the minor histocompatibility antigens.

The antigen which is used to induce an immunostimulation is chosen from any antigen of vaccine interest. It is in particular a tumor antigen or an antigen of a pathogenic agent responsible for acute or chronic infection, known in itself. In a nonlimiting manner, mention may in particular be made of melanoma antigens (Melan-A, Mart1, tyrosinase), epithelial tumor antigens (Her2neu), antigens of viruses (HIV, SIV, hepatitis B and C viruses), Plasmodium antigens, and mycobacterial antigens.

The vectors into which it is possible to insert a sequence of interest in an expression cassette containing the appropriate transcription and translation regulatory elements are known to those skilled in the art. These vectors are constructed by the conventional recombinant DNA and genetic engineering methods, which are known in themselves. Many vectors into which it is possible to insert a nucleic acid molecule of interest in order to introduce it and to maintain it in a eukaryotic host cell are known in themselves; the choice of an appropriate vector depends on the use envisioned for this vector (for example, replication of the sequence of interest, expression of this sequence, maintenance of the sequence in extrachromosomal form or else integration into the host's chromosomal material). It is possible to use, inter alia, naked nucleic acids (linear or circular DNA or RNA), in particular plasmids, and viral vectors such as adenoviruses, retroviruses, lentiviruses and AAVs (adeno-associated viruses), poxviruses, and in particular canarypoxes, herpes viruses and the West Nile virus.

According to a first advantageous embodiment of said use, said modulator defined in a) is a GILZ inhibitor or a recombinant expression vector for the latter, isolated or expressed in modified dendritic cells, and said antigen defined in b) is an antigen of vaccine interest, such as a tumor antigen or an antigen of a pathogenic microorganism, as defined above.

A vaccine for use in the prevention and/or treatment of tumor pathologies and infections is thus obtained, which vaccine is particularly effective insofar as the response against the vaccine antigen is potentiated due to the immunostimulatory properties of said GILZ inhibitor, which are specific for the vaccine antigen. In fact, said inhibitor induces an effective immune response against the antigen by inhibiting the production or the function of regulatory/suppressor T lymphocytes specific for the antigen.

An effective immune response, which does not generate suppressor T lymphocytes or inhibit their function, can be induced in preventive or curative vaccine therapy in order to enhance the immunogenicity of antigenic preparations, for example for anti-infective vaccinations that already exist (... hepatitis B) or are to be identified (hepatitis C, HIV). This possibility of increasing vaccine immunogenicity is particularly advantageous in instances where the vaccine preparation has a weak immunogenicity, or when the individual to be vaccinated suffers from immune deficiency (congenital immune deficiency, chronic renal insufficiency, elderly individual, HIV infection, malaria, measles, etc.).

The enhancement of immunogenicity is also an important objective in the context of antitumor vaccinations, in combination with cell therapy approaches (vaccination with dendritic cells presenting tumor antigens, ex vivo generation of antitumor cytotoxic lymphocytes) or vaccination by injection of tumor extracts or of characterized tumor antigens.

Another application relates to the direct activation of the individual's immune system in the case where its spontaneous response against one or more antigens is insufficient, irrespective of whether or not this insufficient response can be explained by an excess of suppressor T lymphocytes; for example, in the case of an antitumor response, of a chronic infection such as chronic viral hepatitis, HIV infection, herpes virus infections, leprosy, leishmaniosis and malaria.

According to an advantageous arrangement of this embodiment, said inhibitor is a small interfering RNA (siRNA) that targets the GILZ transcript or an antisense oligodeoxynucleotide complementary to said transcript. Preferably, it is an siRNA. By way of non-limiting example, mention may be made of the siRNa corresponding to the sequence SEQ ID NO.: 1.

Vectors that are particularly suitable for the stable expression of siRNAs are in particular those described in T. R. Brummelkamp et al., Science, 2002, 296, 550-553.

According to another advantageous arrangement of this embodiment, said inhibitor is a GILZ antagonist selected from the group consisting of: an antagonist of the akt kinase or an activator of said kinase such as the RANTES chemokine.

Akt kinase antagonists are in particular described in Asselin-Labat et al., mentioned above.

In a second advantageous embodiment of said use, said substance defined in a) is a GILZ protein, a functional fragment of at least 5 consecutive amino acids of said protein, a GILZ activator, or a recombinant expression vector for the above, isolated or expressed in modified dendritic cells, and the antigen defined in b) is selected from the group consisting of: an autoantigen, an allergen, an antigen involved in a chronic inflammatory disease or a transplantation antigen, as defined above.

A medicament for use in the prevention and/or treatment of autoimmune diseases, inflammatory diseases, allergies, transplant rejection and graft-versus-host disease is thus obtained.

Such a medicament induces the expression of GILZ in vivo in dendritic cells and generates antigen-specific regulatory/suppressor T lymphocytes inducing an antigen-specific immune tolerance. These antigen-specific suppressor T lymphocytes are of therapeutic advantage in the course of pathologies characterized by an excess immune response, and for which the triggering antigen has been identified. This is the case, for example, of allogenic or xenogenic transplantation of organs with stem cells, of autoimmune diseases (thyroiditis, diabetes, multiple sclerosis, peripheral neuropathy, celiac disease), of chronic inflammatory diseases (psoriasis, rheumatoid arthritis, inflammatory disease of the digestive tract) or of allergy. This therapeutic effect can be preventative or curative. For example, in organ transplantation, recipient-derived T lymphocytes that suppress a response against the donor can prevent or cure organ rejection. Donor-derived T lymphocytes that suppress a response against the recipient can prevent or cure a graft-versus-host reaction. In the case of allergy, in particular to hymenoptera venoms or to peanuts, of asthma or of other allergic diseases, allergen-suppressing T lymphocytes can prevent the allergic manifestations, the generation of such suppressor T lymphocytes corresponding to a new approach of desensitization against the allergen. This strategy can be adapted according to the discovery of new antigens, in particular new autoantigens.

According to an advantageous arrangement of this embodiment, said GILZ protein defined in a) is the human protein.

According to another advantageous arrangement of this embodiment, said activator is an inducer of GILZ gene expression selected from the group consisting of: dexamethasone, IL-10 and TGFβ.

According to another advantageous arrangement of this embodiment, said antigen defined in b) is selected from the group consisting of: *Phleum pratense, Dermatophagoides pteronyssinus* (Der p 1, Der p 2) and *farinae* (Der f 1), a latex antigen (Hev b 1 to 11), proinsulin, MAG, thyroperoxidase and thyreoglobulin.

According to another advantageous embodiment of said use, said molecule for targeting and/or crossing the plasma membrane of dendritic cells is a ligand of a membrane antigen or receptor selected from the group consisting of: DC-SIGN, CD40, DEC-205, langerin, the mannose receptor and a scavenger receptor. Said ligand is in particular a peptide.

According to another advantageous embodiment of said use, said molecule for targeting and/or crossing the plasma membrane of dendritic cells is an antibody directed against a membrane antigen or receptor selected from the group consisting of: DC-SIGN, CD40, DEC-205, langerin, the mannose receptor and a scavenger receptor.

According to another advantageous embodiment of said use, said vector defined in a) comprises an expression cassette including a promoter for a gene specifically or preferentially expressed in dendritic cells. Preferably, said promoter is the promoter of a gene encoding a protein selected from the group consisting of: DC-SIGN, CD11c, a molecule of the major histocompatibility complex and langerin.

According to another advantageous embodiment of said use, said expression vector defined in a) is a lentivirus.

According to another advantageous embodiment of said use, said GILZ protein or said fragment is in the form of a chimeric protein or peptide that includes the sequence of said peptide for targeting and/or crossing the plasma membrane of dendritic cells and/or the sequence of said antigen of interest defined in b).

According to another advantageous embodiment of said use, said recombinant expression vector defined in a) encodes a chimeric GILZ protein or a chimeric GILZ fragment as defined above.

According to another advantageous embodiment of said use, said antigen defined in b) is loaded onto said modified dendritic cells or is presented by said cells defined in a).

A subject of the present invention is also a medicament comprising at least dendritic cells modified with a molecule selected from the group consisting of: a) a GILZ protein, a functional fragment of at least 5 consecutive amino acids of said protein, a small interfering RNA (siRNA) targeting the GILZ transcript, an antisense oligodeoxynucleotide complementary to said transcript and a recombinant expression vector for the above, as defined above.

According to another advantageous embodiment of said medicament, it comprises an antigen as defined above, preferably said antigen is loaded onto said dendritic cells or is presented by said cells.

A subject of the present invention is also the use of the modified dendritic cells as defined above, for preparing a medicament for use in the prevention and/or treatment of the diseases as defined above.

The dendritic cells are mature or immature, preferably autologous, dendritic cells prepared according to the purification and cell culture techniques known to those skilled in the art. They can be isolated from blood monocytes or from $CD34^+$ cells, derived from umbilical cord blood, from bone marrow or from peripheral blood.

To obtain modified dendritic cells, said substances are introduced into said cells using conventional methods known in themselves: passive diffusion, electroporation, microinjection, association with any substance(s) for targeting and/or crossing the plasma membrane of dendritic cells (membrane peptides, transporters such as nanotransporters, liposomes, nanoparticles, lipids, cationic polymers, ligands, in particular peptides and antibodies specific for surface membrane antigens or receptors as defined above). In addition, these methods can advantageously be combined, for example by using electroporation associated with liposomes.

Advantageously, said substances are coupled to a molecule for targeting and/or crossing the plasma membrane of dendritic cells, in particular in the form of a chimeric protein or peptide or of a recombinant vector encoding said chimeric protein or said chimeric peptide.

A subject of the present invention is also a medicament comprising at least: a) a GILZ protein, a functional fragment of at least 5 consecutive amino acids of said protein, a small interfering RNA (siRNA) targeting the GILZ transcript, an antisense oligodeoxynucleotide complementary to said transcript or a recombinant expression vector for the above, and b) an antigen of interest and/or a molecule for targeting and/or crossing the plasma membrane of dendritic cells, as defined above.

According to an advantageous embodiment of said medicament, it comprises a chimeric GILZ protein or peptide as defined above.

According to another advantageous embodiment of said medicament, it comprises one or more recombinant expression vectors encoding said GILZ protein, said fragment, said siRNA or said antisense oligodeoxynucleotide complementary to said transcript, and said antigen and/or said molecule defined in b).

According to another advantageous embodiment of said medicament, it comprises a recombinant vector encoding a chimeric GILZ protein or peptide as defined above.

In accordance with the invention, the medicaments as defined above can be in the form of a single composition comprising at least one or more substances defined in a) and one or more antigen(s) or molecule(s) for targeting and/or crossing the plasma membrane of dendritic cells, defined in b). Alternatively, they can be in the form of a combined preparation, in which said substance(s) defined in a) and said antigen(s) and/or molecule for targeting and/or crossing the plasma membrane of dendritic cells are used separately or sequentially over time.

The medicaments as defined in the present invention (GILZ protein, modulator or isolated recombinant vector) can be introduced, in vivo, into the target cells (dendritic cells), either by passive diffusion, or using physical methods such as electroporation or microinjection, or by associating it with any substance(s) for targeting and/or crossing the plasma membrane of dendritic cells. Among the substances for crossing the plasma membrane, mention may in particular be made of membrane peptides, transporters such as nanotransporters, liposomes, nanoparticles, lipids or cationic polymers. Among the substances for targeting the plasma membrane of dendritic cells, mention may in particular be made of ligands, in particular peptides and antibodies specific for surface membrane antigens or receptors as defined above. In addition, these methods can advantageously be combined, for example by using electroporation associated with liposomes.

The medicaments as defined in the present invention can in particular be administered directly at their site of action, for example in a tumor or a lymphoid organ, or at the site of administration of a vaccine antigen. Alternatively, they can be integrated into a liposome or a nanoparticle, coated with a ligand or with a monoclonal antibody specific for a surface membrane antigen or receptor of dendritic cells as defined above, so as to be captured by a dendritic cell.

The dosage used varies according to the condition to be treated, the route and the rate of administration, and also the nature and the weight of the species to be treated (human or animal). The product according to the invention is used via the gastrointestinal route (orally, sublingually), parenterally, locally or by intra-site administration. It can be in the form of simple or sugar-coated tablets, of gelatin capsules, of granules, of a syrup, of suppositories, of injectable preparations, of ointments, of creams, of gels or of an aerosol, which are prepared according to the usual methods. In these galenic forms, the product is incorporated into excipients normally used in pharmaceutical compositions, such as talc, gum arabic, lactose, starch, magnesium stearate, cocoa butter, aqueous or nonaqueous carriers, fatty substances of animal or plant origin, paraffin derivatives, glycols, various wetting agents, dispersants or emulsifiers, or preserving agents.

A subject of the present invention is also a method for inducing suppressor/regulatory T lymphocytes in vitro, using a tissue sample containing $CD4^+$ and/or $CD8^+$ T cells, characterized in that it comprises at least:
  a1) preparing autologous dendritic cells expressing the GILZ protein, and, simultaneously or sequentially,
  b1) incubating said dendritic cells defined in a1) with an antigen as defined above and said tissue sample containing said $CD4^+$ or $CD8^+$ T cells.

The dendritic cells expressing the GILZ protein are mature or immature, autologous dendritic cells treated with a GILZ activator as defined above, or else modified with a GILZ protein, a fragment of this protein or an expression vector for the above as defined above; they are prepared as specified above.

The method according to the invention can be used to prepare suppressor/regulatory T lymphocytes in vitro, using a tissue sample containing $CD4^+$ and/or $CD8^+$ T cells, derived from a patient to be treated or from a donor, in the case of transplantation.

Said tissue sample may be peripheral blood, a tumor, bone marrow or any other tissue, in particular a tissue to be transplanted.

Said tissue sample can optionally be cultured, prior to incubation step b).

A subject of the present invention is also the use of regulatory/suppressor T lymphocytes that can be obtained by means of the induction method as defined above, for preparing a medicament for use in the prevention and/or treatment of autoimmune diseases, inflammatory diseases, allergies, transplant rejection and graft-versus-host disease.

A subject of the present invention is also a method for inhibiting suppressor/regulatory T lymphocytes in vitro, using a tissue sample containing CD4+ and/or CD8+ T cells, characterized in that it comprises at least:
- a2) preparing autologous dendritic cells in which the GILZ protein is inhibited, and, simultaneously or sequentially,
- b2) incubating said dendritic cells defined in a2) with an antigen as defined above and said tissue sample containing CD4+ and/or CD8+ T cells.

The dendritic cells in which the expression of the GILZ protein is inhibited are mature or immature, autologous dendritic cells treated or modified with a GILZ inhibitor as defined above, in particular a small interfering RNA (siRNA) or an antisense oligodeoxynucleotide complementary to the GILZ transcript, an expression vector for the above or a GILZ antagonist; they are prepared as specified above.

The method according to the invention can be used to inhibit the function of suppressor/regulatory T lymphocytes in vitro, using a tissue sample as defined above, containing said cells, derived from a patient to be treated.

A subject of the present invention is also the use of regulatory/suppressor T lymphocytes that can be obtained by means of the method of inhibition as defined above, for preparing a medicament for use in the prevention and/or treatment of tumor pathologies and infectious diseases.

According to an advantageous embodiment of said methods, they comprise an additional step consisting in purifying the population of CD4+ or CD8+ T lymphocytes resulting from step b1) or b2) and, optionally, the subpopulation of CD4+ or CD8+ T lymphocytes corresponding to regulatory/suppressor T lymphocytes, using antibodies directed against suitable surface markers (anti-CD25 or anti-GITR, for example).

In addition to the above arrangements, the invention also comprises other arrangements which will emerge from the description that follows, which refers to examples of use of the method which is the subject of the present invention, with reference to the attached drawings in which:

FIG. 1 illustrates the production of GILZ by dendritic cells (DCs). a) Quantitative RT-PCR analysis of the expression of the GILZ gene in dendritic cells treated—by addition to the culture medium—with dexamethasone (Dex (♦), with IL-10 (□) or with TGFβ (▲) on the fifth day of culture (D5) and with CD40 ligand (CD40L), on the seventh day (D7). The values expressed as arbitrary units (AU) correspond to the mean±standard deviation of 3 to 6 independent experiments. b) Flow cytometry analysis of the production of the GILZ protein in nontreated dendritic cells (−) or dendritic cells treated with dexamethasone alone (DEX) or with control small interfering RNA (siRNA) (DEX+control siRNA) or small interfering RNA targeting GILZ (DEX+siRNA GILZ). The curve (✓) represents the labeling with the anti-GILZ polyclonal antibody and the phycoerythrin-coupled secondary antibody (anti-isotype antibody). The curve (*) represents the labeling with the control anti-isotype antibody alone.

Figure 2:
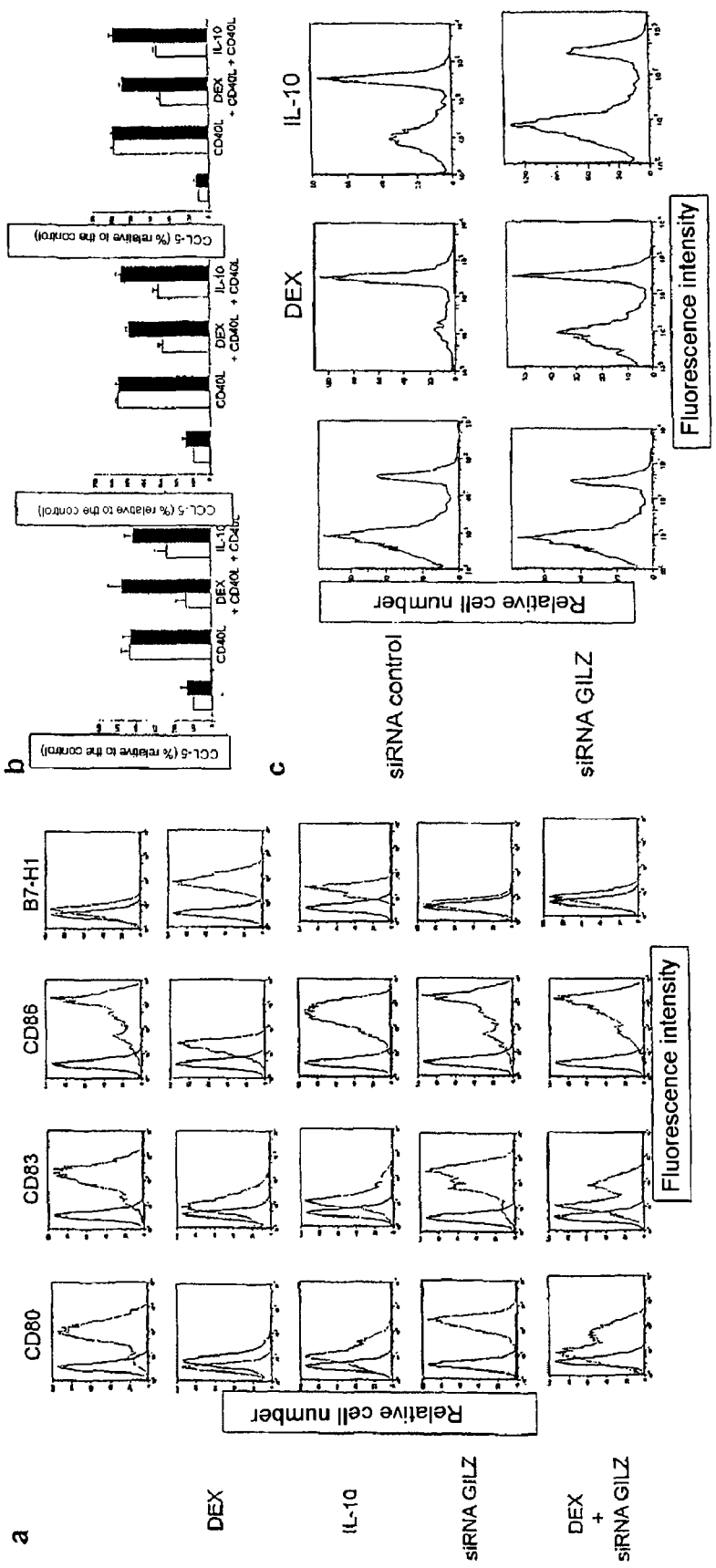

FIG. 2 illustrates the effect of inhibiting the expression of GILZ in the dendritic cells. Mature monocytes derived dendritic cells (MDDCs) were treated on the fifth day of culture (D5) with a control siRNA or an siRNA targeting GILZ (siRNA GILZ) alone, or else with either dexamethasone (DEX) or IL-10, or were nontreated.
- a: CD40L was added on D7 and the phenotype of the dendritic cells was analyzed on D9. The results correspond to an experiment representative of three independent experiments.
- b: CD40L was added on D7 and the production of the chemokines CCL3, CCL5 and CXCL8 was analyzed on D9. The results correspond to the mean±standard deviation of three independent experiments, expressed in the form of percentage relative to the nontreated control dendritic cells. The white bars correspond to the dendritic cells transfected with the control siRNA whereas the black bars correspond to the dendritic cells transfected with the siRNA-GILZ.
- c: The PPD booster antigen (standard proteins purified from *Mycobacterium tuberculosis*) was added on D7 and the autologous CD4+ T lymphocytes on D9. The proliferation of the autologous CD4+ T lymphocytes was analyzed on D14 (one experiment representative of 3 independent experiments). No proliferation is observed in the absence of PPD.

Figure 3:
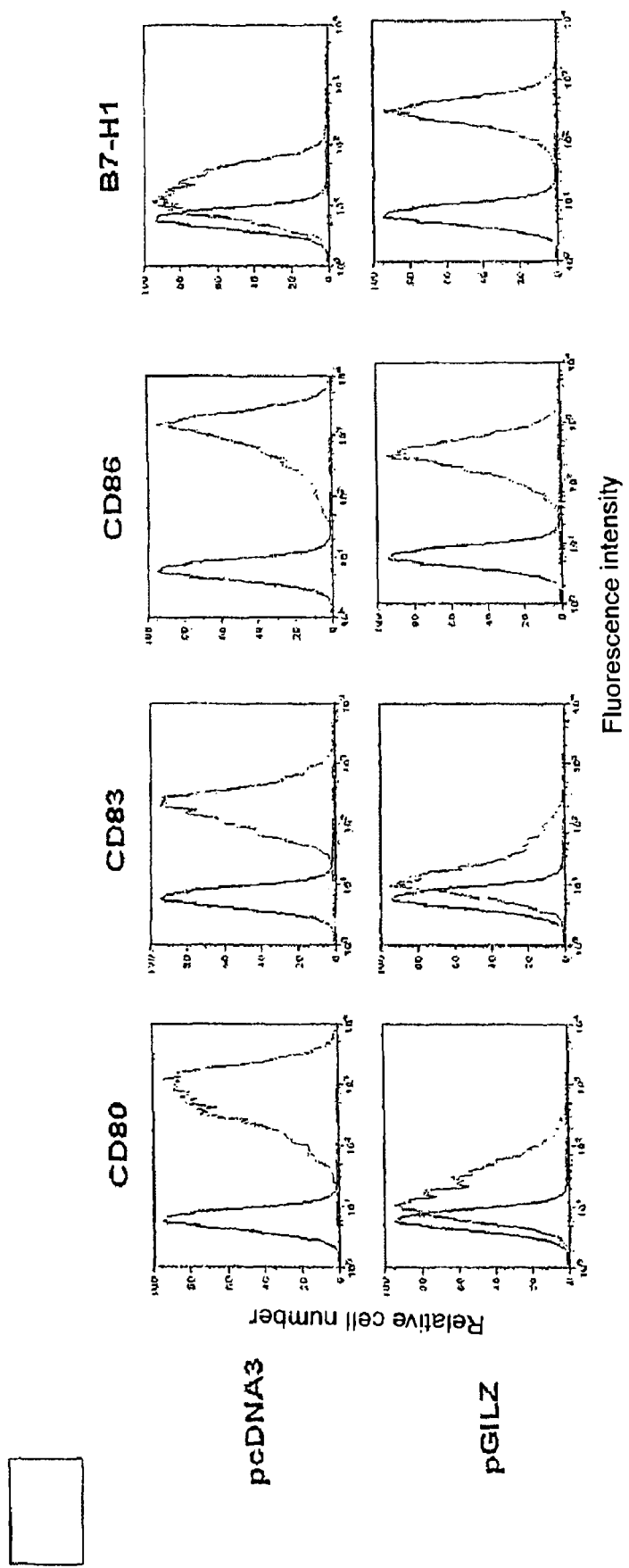

FIG. 3 illustrates the effects of GILZ on the dendritic cells. Mature dendritic cells (MDDCs) were transduced with an empty vector (pcDNA3) or a recombinant vector encoding the GILZ protein (pGILZ) and then stimulated with CD40L. The dendritic cell phenotype was then analyzed by flow cytometry. The results correspond to one experiment representative of two independent experiments.

Figure 4:
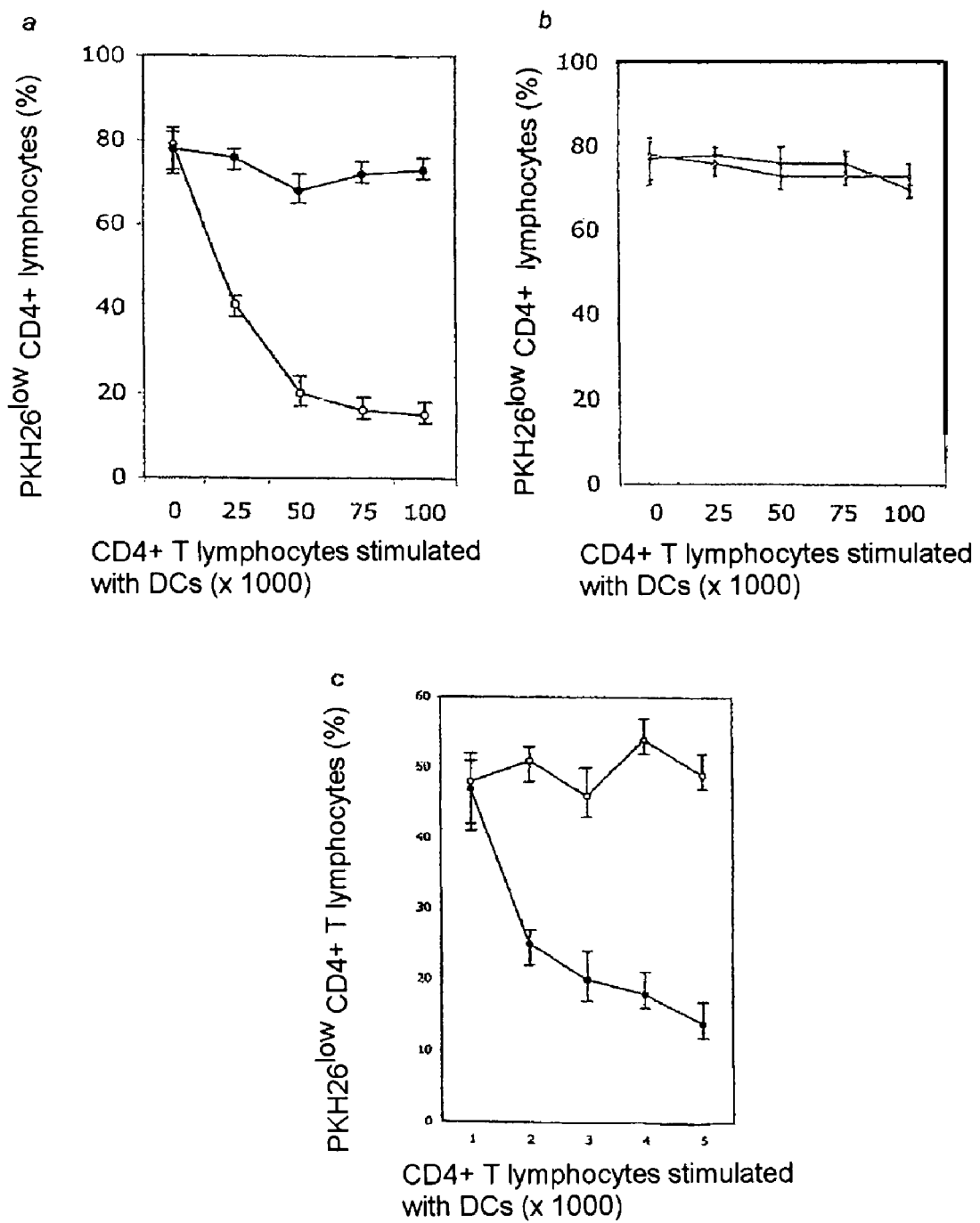

FIG. 4 illustrates the effect of the expression of GILZ on the induction of regulatory T lymphocytes.
- a and b: The effect of the CD4+ T lymphocytes stimulated with dendritic cells loaded with the PPD booster antigen and treated with dexamethasone and a control (♦) or anti-GILZ (○) siRNA was tested on an anti-PPD (a) or anti-CMV (b) proliferative response. The values expressed as percentage relative to the control CD4+ T lymphocytes (stimulated with nontreated dendritic cells) correspond to the mean±standard deviation of 3 independent experiments.
- c: Circulating antigen-presenting cells isolated before or 48 hours after beginning treatment with a glucocorticoid were treated with a control (♦) or anti-GILZ (○) siRNA, loaded with the PPD antigen and used to activate autologous CD4+ T lymphocytes. These lymphocytes were added in increasing number to autologous PBMCs stimulated with the PPD antigen. The results correspond to one experiment representative of two independent experiments.

EXAMPLE 1

Demonstration of the Expression of GILZ in Dendritic Cells

1) Materials and Methods
a) Dendritic Cell Purification and Culture

Immature monocyte derived dendritic cells (iMDDCs) were prepared as described in Palucka et al., J. Immunol., 1998, 160, 4587-4595, apart from minor modifications. Briefly, human monocytes were isolated from the peripheral blood mononucleocell fraction by negative selection, according to the manufacturer's (DYNAL) recommendations. The monocytes (1 to 2×10$^5$ cells/ml) were cultured for 7 days in the presence of GM-CSF and IL-4 (100 ng/ml and 50 ng/ml, respectively, SCHERING-PLOUGH). The maturation of the dendritic cells (MDDCs) was induced in the presence of CD40L (250 ng/ml; IMMUNEX). Dexamethasone (DEX, SIGMA), recombinant human IL-10 (rhIL-10, DNAX) and TGFβ (R&D) were used at the following respective concentrations: 10$^{-7}$ M, 100 ng/ml and 20 ng/ml. For the in vivo experiments, the antigen-presenting cells (APCs) were purified using the monocyte negative selection kit according to the manufacturer's (DYNAL) recommendations.

b) Analysis of GILZ Expression

The expression of the human GILZ gene was analyzed by real time RT-PCR according to the manufacturer's recommendations (Lightcycler™, ROCHE), using the pair of primers described in Berrebi et al. BLOOD, 2003, 101, 729-738 and the human β-actin gene as internal control.

The expression of the human GILZ protein was analyzed by intracellular flow cytometry using an anti-GILZ polyclonal antibody described in Asselin-Labat et al., (BLOOD, 2004, 104-215-) and a phycoerythrin-coupled secondary antibody (BD PHARMINGEN).

c) siRNAs and Transfection

The siRNAs are synthesized by MWG Biotec. The siRNA targeting GILZ (siRNA GILZ) has the sequence 5'-AGUC-CAGGAUUAUAGCCCCdTdT-3' (SEQ ID NO: 1). The control siRNA, consisting of randomly chosen nucleotides, corresponds to a non-relevant siRNA that has no known specificity (5'-ACG GGG GGC CCU UAA AAC AdTdT3', SEQ ID NO: 2).

The siRNA transfection is carried out 48 hours before the end of the iMDDC culture, using the Jetsi endo transfection Kit™ (Q-BIO GENE), according to the manufacturer's recommendations.

2) Results

The expression of the GILZ gene during differentiation of the monocyte derived dendritic cells (MDDCs) was analyzed by RT-PCR (FIG. 1a).

The GILZ gene is expressed in freshly isolated monocytes but its expression disappears after 5 days of culture in the presence of GM-CSF and IL-4 and remains undetectable after the induction of the dendritic cell maturation with CD40L (FIG. 1a).

The addition of dexamethasone (Dex), of IL-10 or of TGFβ on the fifth day of culture stimulates the expression of GILZ, which is detected before and after the treatment with CD40L (FIG. 1a).

Similar results were observed in CD34+-cell-derived dendritic cells.

The production of the GILZ protein was detected, by flow cytometry using an anti-GILZ antibody, only in the dendritic cells treated with dexamethasone, and not in the nontreated control cells (FIG. 1b, upper panel). The expression of the GILZ protein in the dendritic cells treated with dexamethasone is inhibited by an siRNA targeting GILZ (FIG. 1b, lower panel).

EXAMPLE 2

Effect of Dexamethasone-Induced or IL-10-induced GILZ Expression on the Phenotype, the Chemokine Production and the T-Lymphocyte-Stimulating Activity of Dendritic Cells 1) Materials and Methods
a) Analysis of the Dendritic Cell Phenotype The dendritic cell phenotype was analyzed by four-color flow cytometry, using the following monoclonal antibodies: phycoerythrin-coupled anti-CD83 (CD83-PE, COULTER); phycoerythrin-coupled anti-CD80 (CD80-PE, BD BIOSCIENCES); anti-B7-H1 (CLINISCIENCES) and phycoerythrin-coupled anti-CD86 (CD86-PE, BD PHARMINGEN). The anti-B7-H1 antibody is detected using a phycoerythrin-coupled secondary antibody (BD PHARMINGEN).

b) Coculturing of Dendritic Cells and of CD4+ T Cells And Analysis of the CD4+ T Proliferation Immature monocyte-derived dendritic cells (iMDDCs) were treated on the fifth day of culture (D5) with a control siRNA or an siRNA targeting GILZ (siRNA GILZ) alone, or else with either dexamethasone (DEX) or IL-10, or nontreated, and then the PPD booster antigen (standard proteins purified from *M. tuberculosis*, 1 mg/ml, STATENS SERUM INSTITUTE) was added on D7. The dendritic cells ($0.5 \times 10^5$) thus obtained were washed three times and cocultured with $10^5$ freshly purified autologous CD4+ T cells (TCD4 negative selection Kit™, DYNAL) in round-bottomed 96-well culture plates, in RPMI medium supplemented with 10% of human serum group AB. The CD4+ T lymphocyte proliferation was analyzed on the individual level, on the seventh day of coculture (D14), using the dye PKH26, as described in Rimaniol et al., Clin, Exp. Immunol., 2003, 132, 76-80.

c) Cytokine ELISA

The production of chemokines in the culture supernatant of the dendritic cells was analyzed using ELISA kits (R&D SYSTEMS) according to the manufacturer's instructions.

2) Results

The effect of GILZ on the phenotype of the dendritic cells and on the production of chemokines and the stimulation of T lymphocytes by these cells was analyzed.

Dexamethasone and IL-10 modulate dendritic cell maturation; they inhibit the expression of CD80, CD83 and CD86 and they stimulate the expression of B7-H1. These dexamethasone-induced and IL-10-induced phenotypic changes in the dendritic cells are inhibited by the siRNA targeting GILZ (FIG. 2a).

Activation of the dendritic cells with CD40L stimulates the production of the chemokines CCL3, CCL5 and CXCL8. This induction is partially inhibited when the dendritic cells are treated with dexamethasone or IL-10 before the addition of the CD40L. The anti-GILZ siRNA reverses the effect of dexamethasone and of IL-10 on the chemokine production, whereas the control siRNa has no effect (FIG. 2b).

To test the effect of GILZ on antigen presentation, dendritic cells were treated on D5 with a control siRNA or an anti-GILZ siRNA, alone or in the presence of dexamethasone or of IL-10, or were nontreated. Two days later (D7), the PPD booster antigen was added to the dendritic cell cultures. The cells were then washed and mixed with autologous CD4+ T lymphocytes and the proliferation of the CD4+ T lymphocytes was analyzed 7 days later (D14).

The treatment of the dendritic cells with dexamethasone decreases their ability to stimulate CD4+ T lymphocytes. The anti-GILZ siRNA alone or the control siRNA, alone or in the presence of dexamethasone, have no effect on the response of the T lymphocytes. On the other hand, the anti-GILZ siRNA abolishes the effect of dexamethasone on the dendritic cells (FIG. 2c). Similar results were observed with the cells treated with IL-10 in place of dexamethasone.

EXAMPLE 3

Effect of GILZ on Dendritic Cells and Induction of Regulatory T Cells

1) Materials and Methods
a) Recombinant Expression Vector for GILZ and Transfection of Monocyte-Derived Dendritic Cells Dendritic cells were transfected with a recombinant expression vector for GILZ, derived from pcDNA3 (PGILZ; Berrebi et al., mentioned above), or an empty vector (pcDNA3, INVITROGEN), according to the nucleofection transfection protocol, using the AMAXA™ system.

b) Induction of Regulatory T Cells

To evaluate the induction of the regulatory T cells (Tregs), immature monocyte-derived dendritic cells treated on the fifth day of culture (D5) with a controlled siRNA or an siRNA targeting GILZ (siRNA GILZ) alone, or else with either dexamethasone (DEX) or IL-10, or not treated, and then treated with the PPD on D7, were cocultured with CD4+ T cells, as described in example 2. The CD4+ T cells were purified on the seventh day of DC-CD4+ T coculture and added in increasing amounts to $10^5$ autologous PBMCs stimulated with PPD (1 µg/ml, STATENS SERUM INSTITUTE) or the cytomegalovirus (CMV, 25 µg/ml, BEHRING).

2) Results

The phenotypic changes in the dendritic cells, induced with a recombinant expression vector encoding the GILZ protein (pcDNA3-GILZ), were analyzed by flow cytometry, as described in example 2, with the aim of determining whether GILZ, by itself, was capable of reproducing the effects of dexamethasone and IL-10 on the dendritic cells. The dendritic cells transduced with a GILZ expression vector exhibit a phenotype similar to that of the dendritic cells treated with IL-10 or dexamethasone, with weak expression of CD80, CD83 and CD86 and strong expression of B7-H1 (FIG. 3).

The hypothesis that the GILZ-expressing dendritic cells inhibit the CD4+ T lymphocyte response by inducing regulatory T lymphocytes during antigen presentation was verified experimentally. Dendritic cells were treated with a control or anti-GILZ siRNA, alone or with dexamethasone, and with PPD (first culture). After washing, the dendritic cells were used to stimulate autologous CD4+ T lymphocytes. The CD4+ T lymphocytes of this second culture (sensitized CD4+ T lymphocytes) were purified and added in increasing amounts to autologous PBMCs stimulated either with PPD or with CMV (third culture). The CD4+ T lymphocytes sensitized with nontreated dendritic cells or dendritic cells treated with a control siRNA have no effect on the proliferative response of the third culture. CD4+ T lymphocytes sensitized with dendritic cells treated with dexamethasone and with a control siRNA inhibit the anti-PPD response of the third culture, whereas they have no effect on the anti-CMV response. Thus, the dendritic cells treated with dexamethasone induce PPD-specific regulatory T lymphocytes during antigen presentation. The response of this third culture is similar when the CD4+ T lymphocytes are sensitized with dendritic cells treated with dexamethasone and with an anti-GILZ siRNA, or with dendritic cells sensitized with a control siRNA. These results indicate that the inhibition of the GILZ production by the dendritic cells inhibits the ability of the dexamethasone-treated dendritic cells to induce regulatory T lymphocytes (FIGS. 4a and 4b).

The ability of GILZ-expressing antigen-presenting cells (APCs) to induce regulatory T lymphocytes in vivo, was also tested.

The administration of a glucocorticoid to individuals increases the expression of GILZ by their circulating antigen-presenting cells (535±43 arbitrary units (AU) of GILZ mRNA two days after the beginning of the treatment versus 151±35 AU of GILZ mRNA before the administration of glucocorticoid, $p<0.05$). The ability of the circulating antigen-presenting cells of individuals treated with glucocorticoids, to induce regulatory T lymphocytes was tested as described above. In comparison with antigen-presenting cells taken before the beginning of treatment, the antigen-presenting cells of patients treated with glucocorticoids induce CD4+ T lymphocytes that have suppressor functions during a subsequent anti-PPD response, when they are loaded with PPD. Thus, glucocorticoids administered to humans generate, in vivo as in vitro, antigen-presenting cells that induce regulatory T lymphocytes.

The involvement of GILZ in this phenomenon was tested by adding an additional step to the above experiment: the antigen-presenting cells were incubated with a control siRNA or an anti-GILZ siRNA, before the addition of PPD. The induction of regulatory T lymphocytes is completely abolished when the antigen-presenting cells are cultured in the presence of anti-GILZ siRNA (FIG. 4c). Consequently, the treatment of patients with glucocorticoids induces GILZ production by their antigen-presenting cells, and this GILZ expression in vivo is essential for the induction of regulatory T lymphocytes during antigen presentation.

As emerges from the above, the invention is in no way limited to those of its methods of implementation, execution and application that have just been more explicitly described; on the contrary, it encompasses all the variants thereof that may occur to a person skilled in the art, without departing from either the context or the scope of the present invention.

What is claimed is:

1. A method for inducing antigen-specific suppressor/regulatory T lymphocytes in vitro, wherein said antigen is a *Dermatophagoides pteronyssinus* allergen, and wherein said method comprises:
   a1) preparing autologous dendritic cells expressing a GILZ protein; and
   b1) simultaneously or sequentially, incubating said autologous dendritic cells obtained in said preparing a1) with an antigen corresponding to the antigen of said antigen-specific suppressor/regulatory T lymphocytes, and a peripheral blood sample comprising CD4$^+$ T cells.

2. The method according to claim 1, wherein in b1), said autologous dendritic cells are simultaneously incubated with said antigen and said peripheral blood sample.

3. The method according to claim 1, wherein in b1), said autologous dendritic cells are sequentially incubated with said antigen and said peripheral blood sample.

4. The method according to claim 1, wherein said antigen is a *Dermatophagoides pteronyssinus* (Der p 1, Der p 2) allergen.

5. The method according to claim 1, wherein said blood sample is a peripheral blood mononuclear cell (PBMC) sample.

6. The method according to claim 1, wherein said blood sample is an autologous peripheral blood mononuclear cell (PBMC) sample.

\* \* \* \* \*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
aguccaggau uauagcccct t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct
```

-continued

```
<400> SEQUENCE: 2 acgggggggcc cuuaaaacat t                                         21
```